(12) United States Patent
King

(10) Patent No.: US 7,307,721 B2
(45) Date of Patent: Dec. 11, 2007

(54) PARTICLE IMAGING SYSTEM WITH A VARYING FLOW RATE

(75) Inventor: Frederick David King, Richmond (CA)

(73) Assignee: Brightwell Technologies, Ottawa, Ontario (CA)

( * ) Notice: Subject to any disclaimer, the term of this patent is extended or adjusted under 35 U.S.C. 154(b) by 103 days.

(21) Appl. No.: 11/402,931

(22) Filed: Apr. 13, 2006

(65) Prior Publication Data

US 2006/0232780 A1    Oct. 19, 2006

Related U.S. Application Data

(60) Provisional application No. 60/670,670, filed on Apr. 13, 2005.

(51) Int. Cl.
*G01N 15/02* (2006.01)

(52) U.S. Cl. .................... 356/335; 356/436
(58) Field of Classification Search ............. 356/335, 356/436
See application file for complete search history.

(56) References Cited

U.S. PATENT DOCUMENTS

| | | | |
|---|---|---|---|
| 4,979,824 A | 12/1990 | Mathies et al. | 356/318 |
| 5,438,408 A | 8/1995 | Weichert et al. | 356/336 |
| 6,061,130 A | 5/2000 | Plate et al. | 356/335 |
| 6,122,396 A | 9/2000 | King et al. | 382/133 |
| 6,975,400 B2 | 12/2005 | Ortyn et al. | 356/419 |
| 7,016,523 B1 | 3/2006 | Ogawa | 382/133 |
| 2005/0046841 A1 | 3/2005 | Rabinski et al. | 356/336 |
| 2005/0099626 A1 | 5/2005 | King et al. | 356/335 |
| 2005/0109950 A1 | 5/2005 | King | 250/458.1 |
| 2006/0050279 A1 | 3/2006 | Kurozumi et al. | 356/436 |
| 2006/0073585 A1* | 4/2006 | McDevitt et al. | 435/288.7 |
| 2006/0079000 A1* | 4/2006 | Floriano et al. | 436/164 |

\* cited by examiner

Primary Examiner—Roy M. Punnoose
(74) Attorney, Agent, or Firm—Teitelbaum & MacLean; Neil Teitelbaum; Doug MacLean

(57) ABSTRACT

A particle imaging system and a method provided for analyzing particles in a fluid; the system comprising a means for capturing image data of the fluid within a sample cell, and a means for flow control, a valve and a pump, wherein the fluid within the sample cell is periodically stopped, or slowed down, for image capturing and moved rapidly between image capturing events. Advantageously, the present invention allows to increase exposure times, which is particularly significant for fluorescent imaging at low illumination levels.

24 Claims, 3 Drawing Sheets

PARTICLE IMAGING SYSTEM WITH A VARYING FLOW RATE

CROSS-REFERENCE TO RELATED APPLICATIONS

The present invention claims priority from U.S. Provisional Patent Application No. 60/670,670 filed Apr. 13, 2005, entitled "Particle Imaging System Having a Periodically Varying Flow Rate", which is incorporated herein by reference.

FIELD OF THE INVENTION

The present invention relates to measuring a characteristic of a particle or plurality of particles within a sample of a fluid by optical imaging, wherein the fluid flows through a sample cell at a varying rate.

BACKGROUND OF THE INVENTION

Instruments which analyze small particles suspended in liquids in order to provide parameter distribution data or classification of the particle types are of practical importance in fields which include microbiology, medicine, and drinking/wastewater processing. Some of these instruments form images of a volume of liquid along with any particles contained within this volume and analyze these images to obtain the required parameters. In order to analyze a reasonable number of particles in an acceptable time period, the liquid containing the particles is flowed through an optical sample cell at sufficient speed so that successive images (frames) taken by the camera are of fresh material. Since the particles are in motion, each frame must be collected sufficiently quickly so that motion during image capture is controlled to an acceptable level. Rapid image collection requires an adequately fast detector and adequate illumination intensity to achieve an acceptable signal to noise ratio with these detectors.

Detection systems most often employ the use of computers or powerful processor-based systems coupled to one or more charge coupled devices (CCD). CCD or pixel arrays of detecting elements, which detect the presence of one or more particles projected upon a portion of the array of charge coupled elements. Often thousands of frames of information are collected. Within a single frame more than a single particle may be detected; therefore, the software is programmed to find clusters of pixels, indicating the presence of a particle, and to determine a number of pixels, or a pixel total, for the cluster. Some software can determine instances where portions of particles overlap and determine the size of each particle.

Many prior art systems exist for detecting the presence of particles or size of particles in a fluid, such as a supply of potable water. For example, U.S. Pat. No. 5,438,408 entitled "Measuring Device and Method for the Determination of Particle Size Distributions by Scattered Light Measurements" discloses the use of a CCD camera. U.S. Pat. No. 6,061,130 entitled "Apparatus for Determining the Particle Size Distribution of a Mixture" discloses an apparatus that includes a CCD matrix. By identifying particles by predetermined parameters, such as diameter or cross-sectional area, such systems can ascertain the presence or absence of unwanted harmful bacteria in a water sample if a range of diameters of the bacteria is known.

Some of these systems have also been known to be useful in analyzing other fluids such as blood and blood products. Such systems in the area of microbiology and medicine use fluorescent imaging for particle detection and analysis in blood products or other fluids.

Fluorescence is re-emission of light by certain molecules, fluorophores, as they revert to the ground state following excitation by an optical source. The emitted wavelength spectrum is normally longer than the excitation/absorption wavelength spectrum and is characteristic of the molecule being excited. The intensity of fluorescent emission depends on intensity of the excitation light. For the small objects of interest in micro-biological analysis, fluorescence intensity is normally small and high intensity illumination combined with sensitive signal detection is employed.

Fluorescence is commonly employed in microbiological analysis for identification of target entities through detection of naturally occurring fluorophores which they contain. If a target does not contain natural fluorophores, a fluorescent stain or tag may be employed. Different stains are used to selectively label the entity (or parts of the entity) of interest.

In image gathering by static fluorescent microscopy, static samples, positioned on a microscope slide, are illuminated with an excitation light which will be absorbed by the fluorophore. The sample is imaged either by eye or by a camera at a wavelength band corresponding to the emission wavelength. The excitation light is excluded by wavelength selective filtering. Since the target is static, the time taken to acquire the image may be as long as required. The microscope may subsequently be adjusted to obtain a non-fluorescent image of the same target. If this process is carried out manually, scanning a large number of entities is time consuming.

Automatic scanning instruments may consist of microscopes provided with stepwise movement of a slide under computer control. Successive locations on the slide are illuminated, examined for fluorescence and imaged. For example, a microorganism detecting apparatus provided in U.S. Pat. No. 6,122,396 in the names of King, et al. granted on Sep. 19, 2000, comprises a fluorescence microscope and a motor-driven stage assembly for moving a sample slide underneath an imaging subsystem and above an illumination subsystem.

In automatic fluorescent flow cytometry systems, images are not collected but individual detectors are used to detect and measure, in one or more wavelength bands, the total fluorescent emission of target particles suspended in a flowing liquid. This information along with additional, non-fluorescent, morphology measurements, obtained by measuring scattered signals, is used to examine and classify selectively tagged targets commonly consisting of cells or cell fragments.

For example, an optical analytical apparatus is described in U.S. Pat. No. 4,979,824 granted to Mathies et al. on Dec. 25, 1990. This apparatus is based on a flow cytometry system and utilizes a spatial filter to define a small probe volume that allows for detection of individual fluorescent particles and molecules. Laser power and exposure time of the sample are selected to enhance signal-to-noise ratio. Real-time detection of photon bursts from fluorescent particles is used to provide the number, location or concentration of the particles.

For particle imaging systems employing a constant fluid flow, exposure time of a single frame is limited by the effect of streaking when particles within the fluid change their positions significantly during exposure. In order to obtain statistically significant results, it is required that a large number of particles be analyzed in a reasonable period of time, so rates of 1000 to 10,000 particles/sec or more are desirable. High throughput of an imaging system is associated with a high velocity of the fluid, which causes streaking, undesirable and limiting the exposure. The shorter exposure time requires more intense illumination, which, in turn, can adversely affect the sample, especially in applications related to microbiology and medicine.

There are partial solutions known in the art for extending exposure time by electronically compensating for an accurately predetermined object velocity, e.g. the time-delay integration technique used in U.S. Pat. No. 6,975,400 issued to Ortyn, et al. on Dec. 13, 2005.

It is known in the art, that fluorescent imaging requires relatively long exposure thus slowing down flow velocity in a particle imaging system. Moreover, it is advantageous to collect both fluorescent and non-fluorescent images of the same sample, which further decelerates the fluid flow.

An object of the present invention is to provide a method and a system for automatic imaging of particles in a fluid, allowing for long exposure of a sample while providing a high rate of sampling.

SUMMARY OF THE INVENTION

The invention provides a system and method for analyzing particles in a fluid wherein the fluid within the sample cell is periodically stopped, or slowed down, for image capturing and moved rapidly between image capturing events. Advantageously, the present invention allows to increase exposure times to form quality images at a low illumination intensity, which is particularly significant for fluorescent imaging, while acquiring images at a high image capture rate.

One aspect of the invention provides an imaging system for imaging particles in a fluid, the particles characterized by an average diameter or size, the imaging system comprising a sample cell for containing samples of fluid flowing therethrough, an imaging means for sequentially capturing images of particles within the sample cell with a predetermined exposure time per image of at least 1 msec (0.001 second) and an image capture rate of at least 0.1 image per second to obtain a plurality of images, wherein each of the images is characterized by a field of view in the direction of the fluid flow of at least 0.1 mm. The imaging system further comprises a flow control means for slowing down the fluid flow within the sample cell during capturing of the images so that an average displacement of the particles within the field of view in the sample cell in the direction of the fluid flow during each of the image captures is less than 10% of the average particle diameter or size, and for accelerating the fluid flow through the sample cell between capturing the images, so that the fluid within the field of view is substantially replaced between capturing of consecutive two of the plurality of images.

Another aspect of the invention provides a method for obtaining data related to particles in a fluid, the method comprising the steps of: a) providing a fluid sample to a sample cell at a first fluid flow velocity; b) slowing down the fluid flow within the sample cell using a fluid control means so that the fluid flows within the sample cell at a second fluid flow velocity that is at least 100 time smaller than the first fluid flow velocity; c) capturing an image of one or more of the particles within the sample cell during a pre-determined exposure time, the image characterized by a pre-determined field of view in the direction of the fluid flow; d) increasing the fluid velocity within the sample cell to the first fluid velocity for replacing the fluid within the field of view in the sample cell with a new fluid sample; e) repeating steps (b) through (d) a plurality of times at least ones every 10 seconds to obtain a plurality of images; and, f) processing the plurality of images to obtain a characteristic of particle distribution in the fluid; wherein within each step (a) a Reynolds number of the fluid flow in the sample cell is less than 2000, and wherein the second velocity is such that an average displacement of the particles within the field of view in the sample cell in the direction of the fluid flow during each of the image captures is less than 10% of the average particle diameter or size.

BRIEF DESCRIPTION OF THE DRAWINGS

Exemplary embodiments of the invention will now be described in conjunction with the following drawings, in which.

DETAILED DESCRIPTION

Figure 1:
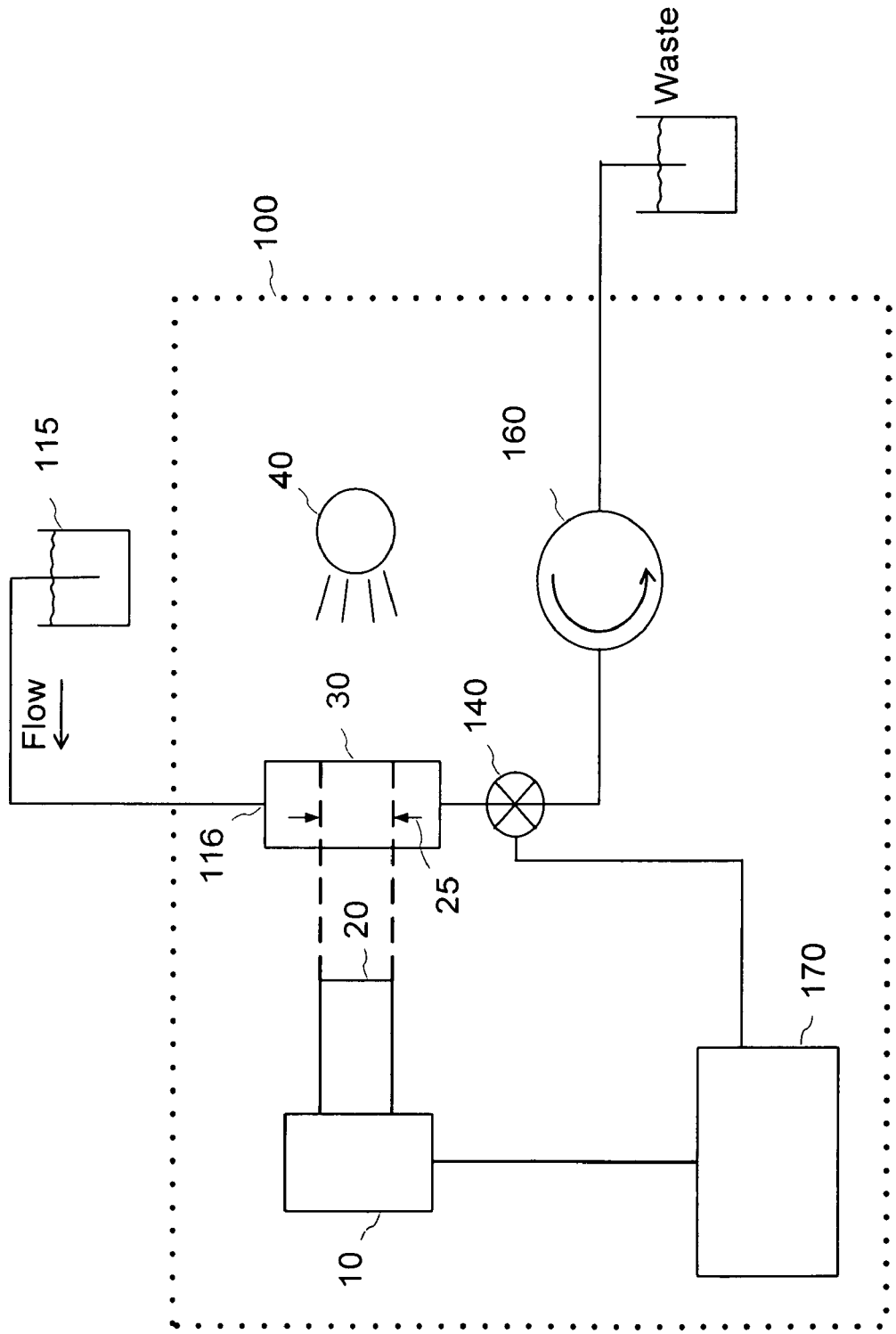
FIG. 1 is a schematic diagram of a particle imaging system according to the present invention.

Exemplary embodiments of the present invention will now be described with reference to FIG. 1. A particle imaging system 100 has a sample cell 30 for containing samples of fluid flowing therethrough, and a conduit 116 for providing samples of the fluid containing suspended particles to be tested into the sample cell 30. The system 100 further includes a flow control means for controllably varying the fluid flow through the sample cell, an imaging means for capturing a plurality of images of the particles within the sample cell, and a processor 170, hereinafter also referred to as a computer 170, for processing the plurality of images to obtain data related to the particles.

In one embodiment wherein the imaging means include a light source 40 disposed outside of the sample cell 30 for illuminating the particles therein, the sample cell 30, also referred to as a flow cell 30 or simply as the cell 30, is substantially transparent for light of the light source 40, or has at least a transparent window for letting the light from the light source 40 therethorough for illuminating and/or imaging the particles within the cell 30.

The conduit 116 is an opening, or a pipe, or the like, which provides a fluid sample with suspended particles from a sample holder 115 to the sample cell 30.

The flow control means comprises a pump 160 and a valve 140, which can be a variable flow valve or a "On-Off" valve, e.g. a solenoid controlled pinch valve or aperture valve providing a response time typically less than 100 milliseconds, and preferably less than 20 milliseconds. The valve should create as little fluid displacement as possible when it closes, since this displacement has to settle in the system before the flow truly stops. The pump 160 for providing the fluid flow can be a peristaltic or syringe type providing flow rates typically in the range of 0.01 to 20 cc/min. In operation, the valve 140 changes a velocity of the fluid flow in a repetitious manner in synchronization with capturing of the images. In a preferred embodiment, both the pump 160 and the flow valve 140 are controlled by the processor 170 to synchronize the fluid flow with capturing of the images.

Within a path of the fluid flow, the valve 140 and the pump 160 can be positioned at either side of the flow cell 30. FIG. 1 shows the valve 140 and the pump 160 placed after the flow cell 30 in a direction of the fluid flow, however it is also possible to place them before the flow cell 30. In both cases the valve 140 is preferably placed between the pump 160 and the cell 30.

The flow control means of another embodiments can exclude the pump while using the valve 140 for flow control, e.g. if the fluid flows through the system 100 under the force of gravity, or were supplied under pressure through the conduit 116. Yet another embodiment can exclude the valve and use the pump 160 having a variable controllable pumping rate and a suitable speed of response, as described hereinabove with reference to the valve 140.

In the shown embodiment, the imaging means comprises the light source 40, an imaging optical system 20 and a camera 10, so that the imaging optics 20 forms an image of the particles in the cell 30 which is captured with the camera 10. The imaging means are characterized by a field of view 25 having a length D in the direction of the fluid flow, so that each of the captured images has information related to particles contained in the fluid in the cell 30 within the field of view. In a preferred embodiment, D is at least 0.1 mm. One skilled in the art will appreciate that larger field of view may be preferred as it enables obtaining images of a greater number of particles during one image capture, however it may also lead to a smaller magnification factor and thus a smaller particle image size. The camera 10, which in some embodiments comprises a single CCD detector or a pixel array of CCD detector elements, or an array of other light detecting elements, is aligned to receive light from the light source 40 after it passed through the cell 30. The light source 40 can be a lamp, a light-emitting diode, or other suitable light emitting device. The imaging optical system 20, e.g. a commercially available microscope objective, is disposed between the sample cell 30 and the CCD camera 10 to collect at least a portion of the light passed through the cell 30 and to focus it onto the CCD detector elements.

Figure 2:
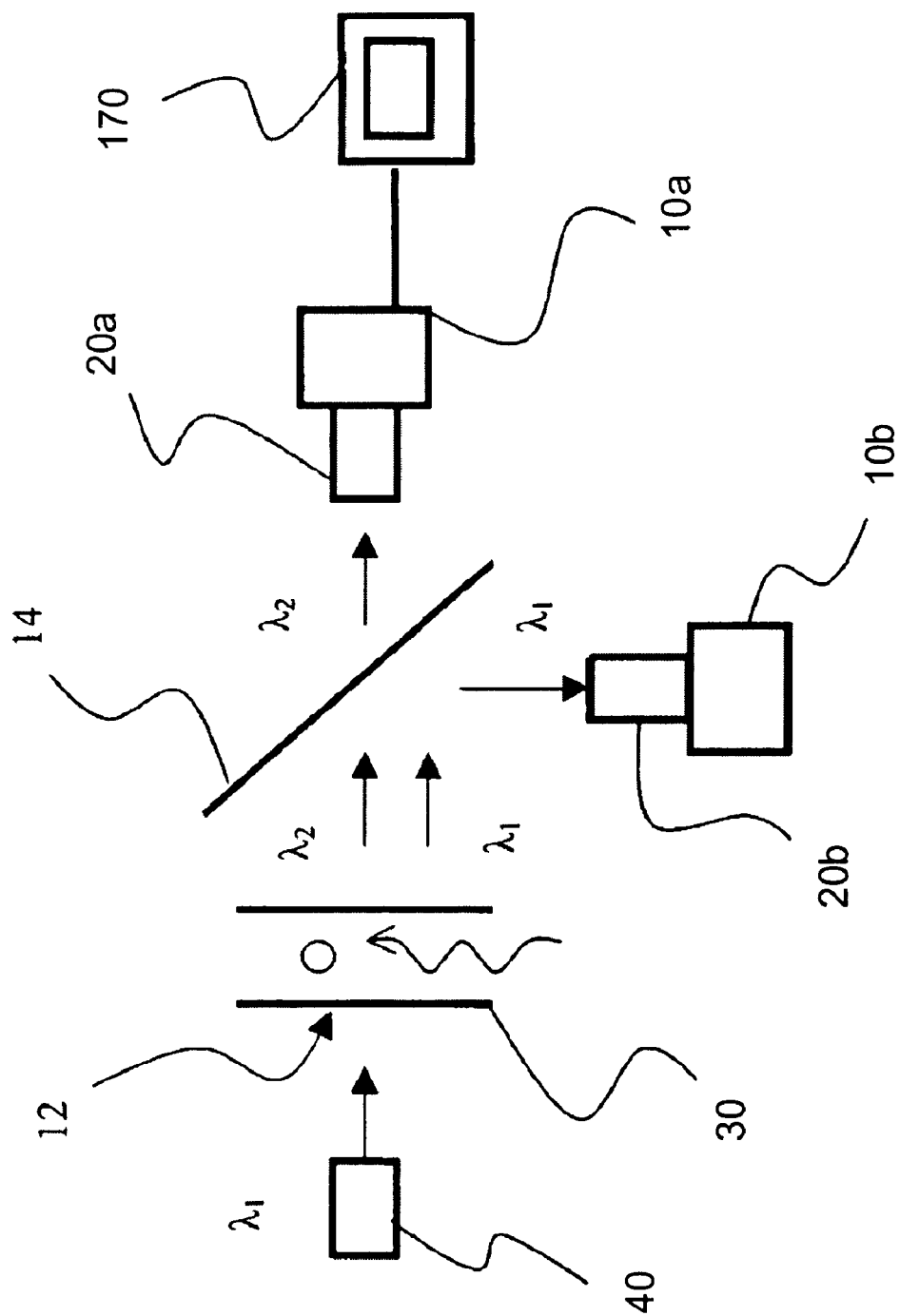
FIG. 2 is a schematic diagram of an imaging means of the particle imaging system in one embodiment thereof.

Another example of the imaging means for use in the system of the present invention is disclosed in US Application 2005/0109950, which is assigned to the assignee of the present invention and is incorporated herein by reference. Said imaging means, illustrated by FIG. 2, comprises a light source 40, an optical filter 14, two cameras 10a and 10b, and two magnification systems 20a and 20b. In this embodiment, the particles suspended in the fluid are fluorescent, e.g. have been fluorescently tagged prior to entering the cell 30, or comprise naturally occurring fluorophores. The light source 40 continually emits pulses of light at a first wavelength $\lambda_1$ at an optical excitation zone 12 of the sample cell 30. The previously fluorescently tagged particles or naturally occurring fluorophores absorb some of the light at $\lambda_1$ and emit light at the fluorescence emission wavelength $\lambda_2$. The fluorescence emission wavelength $\lambda_2$ passes through the optical filter 14, permitting only a narrow band of wavelengths at or near the fluorescent wavelength $\lambda_2$ to pass to a first digital camera 10a via a magnification system 20a. The remaining light at the first wavelength $\lambda_1$ is reflected off of the optical filter 14 to a second digital camera 10b via a second magnification system 20b. If the cameras have electronic shutters, the light source 40 could simply emit light continually. The number, intensity and location of pixels, which detect fluorescent and not fluorescent signals on first and second images in the first and second cameras 20a and 20b, respectively, are recorded by system software in a computer 170.

In operation, a liquid sample with particles flows through the sample cell 30 at a varying flow rate. A plurality of successive images of particles in the sample cell, said images also referred to herein as frames, is used to determine the particle parameter distributions and to capture selected images in statistically significant volumes of liquid, as defined by the field of view of the imaging system 20 and a depth of the cell 30. The particle parameter under consideration may be one of several possible parameters; for example cross-section, shape, or a particular bacteria, which corresponds to a predetermined cross-section range. For example, if bacteria B is known to be within a predetermined diameter or size range, then detecting the numbers of bacteria B in a sample may be the desired goal.

According to the present invention, the flow control means 140, 160 moves the fluid through the sample cell in a time varying manner such that the fluid flow is repeatedly slowed down, and between two consecutive slow-downs the fluid flow is accelerated to substantially replace the fluid sample in the sample cell with a new fluid sample. The slow-downs should be understood as periods of time when the fluid is substantially at rest or flows slowly, having an average velocity at least 100 times and preferably 1000 times less than the average velocity of the fluid in periods between two slow-downs, or having a first fluid flow velocity while replacing the fluid sample that is at least 100 times, and preferably 1000 times, higher than a second fluid flow velocity between two slow-downs.

Preferably, the processor 170 synchronizes the flow control means and the imaging means in such a way that the fluid sample is stopped, or its flow through the cell 30 is significantly slowed down, during frame capture and moved rapidly between frames so that a new fluid sample is presented in the next frame.

Preferably, the fluid flow should be laminar in order to avoid streaking resulting from turbulent motion. The flow will be normally laminar if the Reynolds number of the fluid in the sample cell is less than 2000. It is desirable to change the flow velocity from slow to fast over a short time period, preferably in the order of tens of milliseconds or less, while avoiding turbulence when the flow is slow. The present invention takes advantage of the fact that a laminar flow responds rapidly to downstream or upstream changes in flow rate and remains laminar, i.e. rapid changes in the flow rate may be achieved without inducing turbulence. In some embodiments it is therefore preferred that the Reynolds number of the fluid flow stays below 2000 also during the time intervals between frame captures when the cell 30 is being re-filled, and the flow rate is relatively high. In order to keep the flow laminar for a wide range of velocities, a flow cell of the present invention preferably has a small depth between 20 and 1000 microns. By way of example, for water and liquids having viscosities comparable to water, the depth of the flow cell between about 100 and 400 microns is preferable for the velocities between 0.001 mm and 100 mm/sec.

Advantageously, by slowing down the fluid during capturing the images, and accelerating the fluid between capturing the images, the particle imaging system of the present invention enables to realize both a high image capture rate $R_{image}$, thereby enabling a high data rate collection, and a high exposure time $\tau$ per image for improved image quality and contrast at low illumination levels.

By way of example, we will compare a conventional particle imaging system employing a constant fluid flow to a system of the present invention employing an intermittent fluid flow. Each of the two systems employs a camera 10 processing images at a rate $R_{image}$=5 frames per second and providing 5 times magnification for a 2000×2000 micron field of view, i.e. D=2 mm. For the constant flow system, a flow velocity $R_{flow}$ of at least $R_{image} \cdot D = 10$ mm/sec is required to provide new fluid samples in successive frames. However, if the fluid flows during the image capture, the particles are displaced during exposure leading to so called "streaking" in the images, i.e. an elongation of the particle images in a direction corresponding to the fluid flow by a streaking length $s = \tau \cdot R_{flow}$, where $\tau$ is the exposure time during which the image is capture by the photodetecting element of the camera 10. If a maximal allowed displacement s of a particle during exposure is 10% of an average diameter d or size of the particle, and d=0.5 micron, the maximum exposure time $\tau$ must be less than $d/(R_{image} \cdot D) = 50$ microseconds.

The system of the present invention provides the intermittent fluid flow, for example as follows: the fluid flows at 20 mm/sec or more for 100 milliseconds in order to provide a new fluid sample to the sample cell; then the flow is stopped, and a 50 millisecond waiting period allows particles in the sample cell to come to stationary equilibrium; after the waiting period the sample of the liquid is imaged with the 50 millisecond exposure. The cycle is repeated. The exposure time provided by the system of the present invention with the intermittent fluid flow is 50 millisecond. This constitutes a 1000 times increase in exposure time over the constant flow prior art system.

Figure 3:
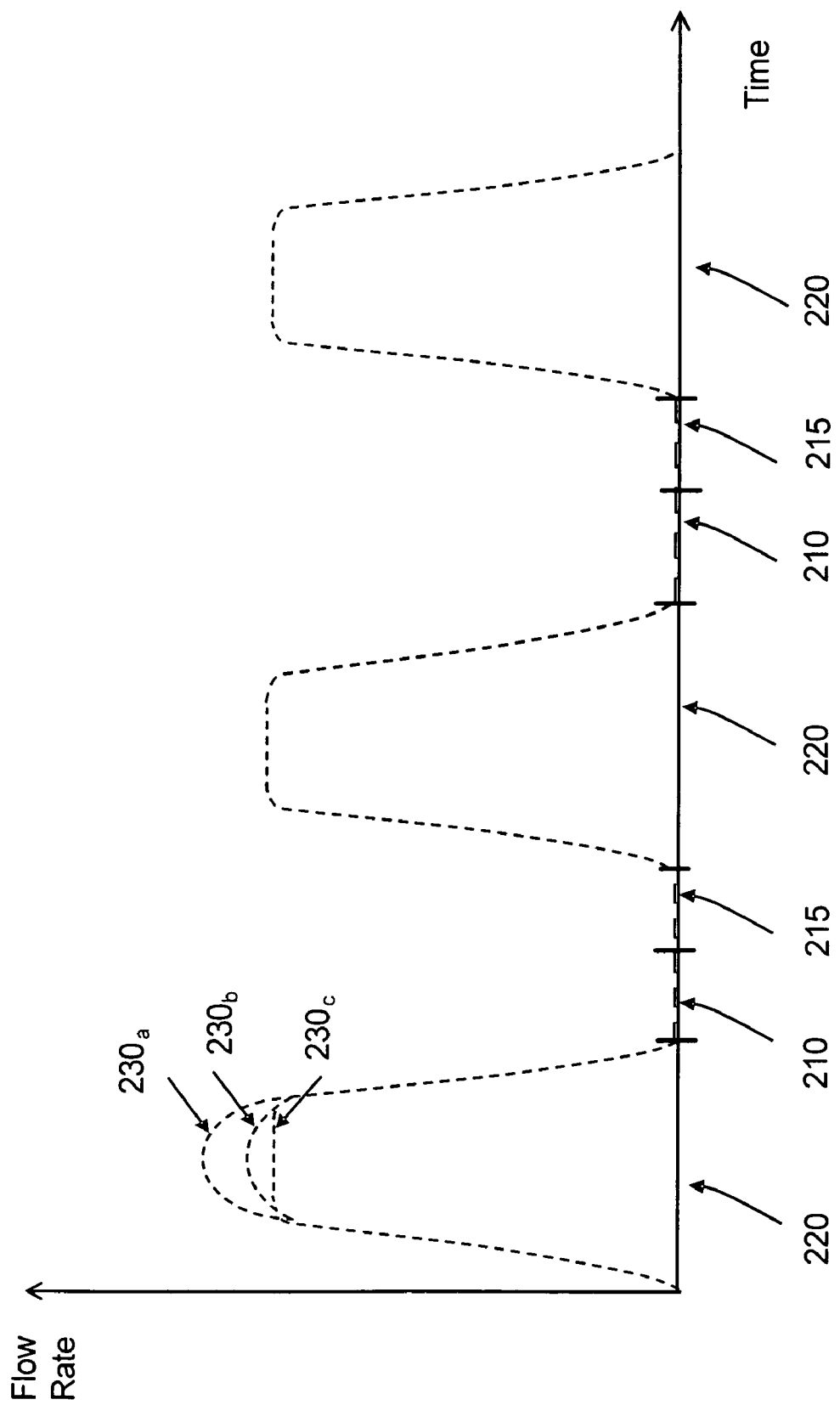
FIG. 3 is a plot of a flow velocity vs. time in a periodic mode of operation of the present invention.

FIG. 3 is a plot of the flow rate vs. time according to the aforedescribed example. The varying flow rate is controlled by the computer and is periodic in this embodiment; however it can be also aperiodic in other embodiments. The figure shows an image capturing interval 215, a sample replacement interval 220 and a waiting interval 210. During the waiting periods 210 and exposure 215 the fluid in the sample cell is substantially at rest, and during intervals 220 the flow rate is relatively high to provide a replacement of the fluid sample in the flow cell with a new fluid sample. The flow velocity may have various profiles during interval 220, as shown in FIG. 3 by arrows 230a-c.

In the aforedescribed example, efforts are taken to keep turbulence of the fluid in the flow cell low during a first interval 215 while the images are captured. A length of the first interval is 50 milliseconds and velocity of the flow is around zero. During a second interval, comprising replacement time 220 and waiting time 210, the flow of the fluid may be turbulent however no images are captured within the second interval. The second interval length is 150 milliseconds and has an average velocity of the flow around (or more) 1.3 cm/sec.

Since the waiting periods 210 are designed to reduce turbulence in the sample cell, a length of the waiting periods 210 depends on physical properties of the fluid with suspended particles as well as geometry of the system and the velocity of the flow. Particular conditions may render the waiting periods optional. In a preferred embodiment, the fluid flow is controlled so that the Reynolds number is at most 2000 or less throughout the image capturing and refilling process to minimize the waiting time interval 210.

In some embodiments, the fluid does not stop entirely during the slow-downs 210, but moves slower than during periods 220. Preferably, during the entire process of capturing of the images the fluid flow is controlled so to periodically vary the velocity of fluid flow through the sample cell between a minimum fluid velocity of at most 0.1 mm/sec and a maximum fluid velocity of at least 1 mm/sec.

In order to obtain a statistically significant number of images within a reasonable period of time, the system of the present invention has the image capture rate $R_i$ of at least 0.1 image per second, and preferably at least one image per second. The system provides a speedy replacement of a fluid sample within a field of view of the image capturing means and an advantageously long exposure time $\tau$, of at least 1 msec and preferably at least 0.02 seconds. The exposure time $\tau$ per image capture is of at least $0.1/R_i$, i.e. both the image capture rate and the image capture time are both suitably large, and the image capture time is at least 10% of the image capture period; a constant flow in a prior art system would typically require much smaller relative exposure time to avoid streaking.

Since the fluid is moving slowly during the image capture, the average displacement of the particles in the direction of the fluid flow is preferably less than 10% of the average particle diameter, so to make the streaking relatively small and to enable suitably accurate detection of particle sizes. Without referring to the particle size, in preferred embodiments of the current invention the average displacement s during each of the image captures is less than 10% of the product of the image capture rate $R_i$, the exposure time $\tau$, and the field of view D, i.e. $s < 0.1 \cdot \tau \cdot R_i \cdot D$, which ensures that the present invention yields at least 10 time smaller streaking than a similar conventional constant-flow imaging systems having the same image capture rate.

The processor 170 can be programmed to control at least the camera 10, or both the camera 10 and the valve 140, so to synchronize the flow control means and the imaging means so that the images are captured during first time intervals wherein the fluid flow is substantially slowed down so that the average displacement of the particles within the field of view in the sample cell is suitably small, and the fluid flow is accelerated during second time intervals between the first time intervals so that during each of the second time intervals a fluid sample within the field of view in the sample cell is replaced with a new fluid sample, with an average flow velocity within the first time intervals being preferably at least 100 times less than an average flow velocity within the second time intervals.

In some embodiments, the flow control means, e.g. the valve 140, periodically varies the velocity of the fluid flow between a minimum fluid velocity of at most 0.1 mm/sec and a maximum fluid velocity of at least 1 mm/sec. By way of example, for liquids having viscosities comparable to water and the exposure time of 50 milliseconds, an average velocity of the flow during period 210 is less than 0.05 mm/sec and preferably less than 0.005 mm/sec ensuring that no significant streaking will be observed during frame capture. An advantage of operating with some remaining motion during exposure is in reduction of the waiting period and/or the time interval between capturing of the images.

Of course numerous other embodiments may be envisioned without departing from the spirit and scope of the invention.

I claim:

1. An imaging system for imaging particles in a fluid, the particles characterized by an average diameter or size, the imaging system comprising:

a sample cell for containing samples of fluid flowing therethrough;

an imaging means for sequentially capturing images of particles within the sample cell with a pre-determined exposure time per image of at least 1 msec and an image capture rate of at least 0.1 image per second to obtain a plurality of images, wherein each of the images is characterized by a field of view in the direction of the fluid flow of at least 0.1 mm;

a flow control means for slowing down the fluid flow within the sample cell during capturing of the images so that an average displacement of the particles within the field of view in the sample cell in the direction of the fluid flow during each of the image captures is less than 10% of the average particle diameter or size, and accelerating the fluid flow through the sample cell between capturing the images, so that the fluid within the field of view is substantially replaced between capturing of consecutive two of the plurality of images.

2. An imaging system of claim 1 wherein the fluid flow within the sample cell at any time between and during capturing of the images is characterized by a Reynolds number of less than 2000.

3. An imaging system of claim 2 wherein the sample cell has a depth between 20 and 1000 microns.

4. An imaging system of claim 3 wherein the depth of the sample cell is between 100 and 400 microns.

5. An imaging system of claim 2 wherein an average velocity of the fluid in the sample cell during the image captures is at least 100 times less than an average velocity of the fluid during time intervals between capturing of the images.

6. An imaging system of claim 5 wherein the average fluid velocity in the sample cell during the image capture is at least 1000 times less than the average fluid velocity during time intervals between capturing of the images.

7. An imaging system of claim 2 wherein the fluid in the sample cell is substantially at rest during capturing of the images.

8. An imaging system of claim 2 wherein the image capture rate is at least one image per second.

9. An imaging system of claim 2 wherein the exposure time per image is at least 0.02 seconds.

10. An imaging system of claim 1 wherein the flow control means comprises a flow valve for changing the flow velocity.

11. An imaging system of claim 10 wherein the flow valve has a response time less than 100 milliseconds.

12. An imaging system of claim 11 wherein the flow valve has a response time less than 20 milliseconds.

13. An imaging system of claim 1 wherein the flow control means comprises a pump for providing the fluid into the fluid cell and for changing the fluid velocity.

14. An imaging system of claim 1 wherein the imaging means comprises a pixel array of detector elements for capturing the images, and imaging optics for forming the images on the pixel array of detector elements.

15. An imaging system of claim 1 wherein the flow control means is for periodically varying the velocity of fluid flow through the sample cell between a minimum fluid velocity of at most 0.1 mm/sec and a maximum fluid velocity of at least 1 mm/sec.

16. An imaging system of claim 1 wherein the sample cell has at least a transparent window for illuminating and/or imaging the particles therethrough.

17. An imaging system for imaging particles in a fluid, the system comprising:

a sample cell for containing samples of fluid flowing therethrough;

a flow control means for controllably varying the fluid flow through the sample cell;

an imaging means for sequentially capturing a plurality of images of particles within the sample cell at a pre-determined image capture rate $R_{image}$ of at least 0.1 frame per second with an exposure time $\tau$ per image capture of at least $0.1/R_{image}$, the images characterized by a field of view of length D in the direction of the fluid flow;

a processor for synchronizing the flow control means and the imaging means so that the images are captured during first time intervals wherein the fluid flow is substantially slowed down so that an average displacement of the particles within the field of view in the sample cell in the direction of the fluid flow during each of the image captures is substantially less than $0.1 \cdot R_{image} \cdot D \cdot \tau$, and the fluid flow is accelerated during second time intervals between the first time intervals so that during each of the second time intervals a fluid sample within the field of view in the sample cell is replaced with a new fluid sample; and, wherein an average flow velocity within the first time intervals is at least 100 times less than an average flow velocity within the second time intervals.

18. A method for obtaining data related to particles in a fluid, the particles characterized by an average diameter or size, the method comprising the steps of:

a) providing a fluid sample to a sample cell by flowing the fluid therethrough at a first fluid flow velocity;

b) slowing down the fluid flow within the sample cell using a fluid control means so that the fluid flows within the sample cell at a second fluid flow velocity that is at least 100 time smaller than the first fluid flow velocity;

c) capturing an image of one or more of the particles within the sample cell during a pre-determined exposure time, the image characterized by a field of view in the direction of the fluid flow;

d) increasing the fluid velocity within the sample cell to the first fluid flow velocity for replacing the fluid within the field of view in the sample cell with a new fluid sample;

e) repeating steps (b) through (d) a plurality of times at least ones every 10 seconds to obtain a plurality of images; and, f) processing the plurality of images to obtain a characteristic of particle distribution in the fluid;

wherein during step (a) a Reynolds number of the fluid flow in the sample cell is less than 2000, and wherein the second fluid flow velocity is such that an average displacement of the particles within the field of view in the sample cell in the direction of the fluid flow during each of the image captures is less than 10% of the average particle diameter or size.

19. A method according to claim 18 wherein the second fluid flow velocity during the image capture is at least 1000 times less than the first fluid flow velocity.

20. A method of claim 18 wherein in step (c) the fluid sample is substantially at rest within the sample cell.

21. A method of claim 20 wherein step (c) comprises waiting a predetermined period of time for the fluid within the sample cell to come to rest prior to capturing the image.

22. A method of claim 18 wherein the fluid flow is periodic.

23. A method of claim 18 wherein step (c) comprises illuminating the sample cell with an optical source at a first wavelength causing the particles to emit fluorescent light at a second wavelength; and forming the image of one or more of the particles within the sample cell with the fluorescent light at the second wavelength.

24. A method of claim 18 wherein:
   steps (a)-(d) are repeated at least once per second for a plurality of times to collect the plurality of images at an image capture rate of at least one image per second,
   the pre-determined exposure time is at least 1 msec for providing suitable image quality, and
   average displacement of the particles within the field of view in the sample cell in the direction of the fluid flow during each of the image captures is less than 10% of the product of the image capture rate, the exposure time and the field of view in the direction of the fluid flow.

* * * * *